(12) United States Patent
Wheatley (10) Patent No.: US 9,655,524 B2
(45) Date of Patent: May 23, 2017

(54) OCT PROBE WITH BOWING FLEXOR

(71) Applicant: NOVARTIS AG, Basel (CH)

(72) Inventor: Barry Lynn Wheatley, Ocenaside, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/267,692

(22) Filed: May 1, 2014

(65) Prior Publication Data

US 2015/0080719 A1    Mar. 19, 2015

Related U.S. Application Data

(60) Provisional application No. 61/877,368, filed on Sep. 13, 2013.

(51) Int. Cl.
*A61B 5/00* (2006.01)
*A61B 1/07* (2006.01)

(52) U.S. Cl.
CPC .............. *A61B 5/0066* (2013.01); *A61B 1/07* (2013.01); *A61B 5/0084* (2013.01)

(58) Field of Classification Search
CPC ....... A61B 1/07; A61B 5/0066; A61B 5/0084; A61M 5/14546; A61M 5/14566
See application file for complete search history.

(56) References Cited

U.S. PATENT DOCUMENTS

| 5,905,829 | A | 5/1999 | Maenishi |
| 6,066,102 | A | 5/2000 | Townsend |
| 6,402,719 | B1 | 6/2002 | Ponzi |
| 6,485,413 | B1 * | 11/2002 | Boppart ............. A61B 1/00096 356/450 |
| 6,564,087 | B1 | 5/2003 | Pitris et al. |
| 7,616,986 | B2 | 11/2009 | Seibel |
| 2001/0023346 | A1 | 9/2001 | Loeb |
| 2001/0055462 | A1 | 12/2001 | Seibel |
| 2002/0003915 | A1 * | 1/2002 | Sorin ....................... G02B 6/14 385/7 |
| 2002/0111548 | A1 | 8/2002 | Swanson et al. |
| 2004/0151441 | A1 * | 8/2004 | Bennett ................ G02B 6/4224 385/92 |

(Continued)

FOREIGN PATENT DOCUMENTS

EP    1769734 A1    4/2007

OTHER PUBLICATIONS

International Search Report and Written Opinion for PCT/US2014/051092, Not yet published, 8 pages, dated Dec. 11, 2014.

(Continued)

*Primary Examiner* — Baisakhi Roy
(74) *Attorney, Agent, or Firm* — Darien Reddick (57) ABSTRACT

An OCT probe includes a cannula and includes a selectively displaceable light-carrying optical fiber disposed within the cannula. The optical fiber may be arranged to emit light from a distal end thereof. A flexor may be bent to divide the flexor into a first segment and a second segment extending along a lumen of the cannula. The first segment may be coupled to the optical fiber. A driver may be configured to push or pull the second segment in the axial direction to elastically bow the second segment and laterally displace the optical fiber to perform an OCT scan.

20 Claims, 9 Drawing Sheets

(56) References Cited

U.S. PATENT DOCUMENTS

| | | | |
|---|---|---|---|
| 2005/0004453 A1* | 1/2005 | Tearney | A61B 5/0066 600/427 |
| 2005/0078910 A1 | 4/2005 | Hickingbotham | |
| 2006/0170930 A1 | 8/2006 | Li | |
| 2006/0262379 A1* | 11/2006 | Choo | G02B 6/3566 359/290 |
| 2007/0066983 A1 | 3/2007 | Maschke | |
| 2007/0284516 A1 | 12/2007 | Bustamante et al. | |
| 2008/0080206 A1 | 4/2008 | Charles | |
| 2008/0177183 A1 | 7/2008 | Courtney et al. | |
| 2008/0243031 A1 | 10/2008 | Seibel | |
| 2009/0028407 A1 | 1/2009 | Seibel et al. | |
| 2009/0198125 A1 | 8/2009 | Nakabayashi et al. | |
| 2009/0208143 A1 | 8/2009 | Yoon et al. | |
| 2009/0268161 A1* | 10/2009 | Hart | A61B 3/102 351/208 |
| 2010/0228119 A1* | 9/2010 | Brennan | A61B 5/0066 600/424 |
| 2011/0275890 A1 | 11/2011 | Wang et al. | |
| 2012/0029354 A1 | 2/2012 | Mark et al. | |
| 2012/0310042 A1 | 12/2012 | Joos et al. | |
| 2012/0330101 A1 | 12/2012 | Brennan et al. | |
| 2015/0080718 A1* | 3/2015 | Wheatley | A61B 1/07 600/429 |

OTHER PUBLICATIONS

International Search Report and Written Opinion for PCT/US2014/04072, dated Oct. 20, 2014, 9 pages.
European Search for Application No. 14843997.9, Publication No. EP30314319, Published May 4, 2016, 4 pages.
PCT International Preliminary Report on Patentability, PCT/US2014/040742 , Mar. 22, 2016, 8 pages.

* cited by examiner

OCT PROBE WITH BOWING FLEXOR

CROSS-REFERENCE TO RELATED APPLICATIONS

This Application claims the benefit of U.S. Provisional Application No. 61/877,368, filed Sep. 13, 2013, the entire contents of which are incorporated herein by reference.

TECHNICAL FIELD

The present disclosure relates to apparatuses and methods for scanning tissue with an OCT probe, and more particularly, to apparatus and methods that have a displaceable fiber.

BACKGROUND

Optical Coherence Tomography (OCT) systems are used to capture and generate three-dimensional images of patient tissue layers. These systems include OCT probes that often invasively penetrate tissue to obtain visualization of tissue within a patient. In ophthalmology, OCT probes are used to obtain detailed images of tissue about the eye or even forming a part of the eye, such as the retina.

In use, an optical light beam is directed through the probe at the tissue. A small portion of this light reflects from sub-surface features of the tissue and is collected through the same probe. Most light is not reflected but, rather, diffusely scatters at large angles. In conventional imaging, this diffusely scattered light contributes background that obscures an image. However, in OCT, a technique called interferometry records the optical path length of received photons, and provides data that reject most photons that scatter multiple times before detection. This results in images that are more clear and that extend in the depth of the tissue.

SUMMARY

In an exemplary aspect, the present disclosure is directed to an OCT probe for imaging patient tissue. The OCT probe includes a cannula having a lumen and having a cannula axis. The OCT probe also includes a selectively displaceable light-carrying optical fiber disposed within the lumen and having a distal end. The optical fiber may be adapted to emit light from the distal. A flexor extends through the lumen and includes a first segment and a second segment. The first segment may be coupled to the optical fiber. A driver may be configured to axially displace the second segment such that the optical fiber is laterally displaced.

In an aspect, the flexor comprises a bend, and the second segment extends from the bend in an oblique direction. In an aspect, the second segment is configured to bow when the driver displaces the second segment in a first axial direction. In an aspect, the flexor includes a biasing element that cooperatively biases the optical fiber to a position in the cannula.

In an aspect, a second flexor may be included. The second flexor may extend through the lumen and include a third segment and a fourth segment. The third segment may be coupled to the optical fiber on a side of the optical fiber opposite the first segment. In an aspect, the driver may be operatively coupled with the second segment and the fourth segment and configured to alternatingly displace one of the second segment or fourth segment in a first axial direction and the other of the second segment or fourth segment in a second axial direction opposite the first axial direction. In an aspect, the second flexor may include a bend, and the fourth segment may extend from the bend in an oblique direction. The fourth segment may be configured to bow when the fourth segment is displaced in one of the first axial direction or the axial direction.

In an aspect, the driver is configured to displace the first segment in a first axial direction while displacing the second segment in a second axial direction opposite the first axial direction to cause the optical fiber to be laterally displaced. In an aspect, the first segment may be shorter than the second segment. In an aspect, a lens may be disposed in the lumen of the cannula distal of the optical fiber and moveable with the fiber. In an aspect, the cannula may be sized to penetrate an eye of a patient to scan a retina of the eye.

In an aspect, the flexor may include a substantially tubular portion and the second segment may extend through the tubular portion. In an aspect, the tubular portion may be fixed in place relative to the cannula. In an aspect, the first segment may be coupled to the optical fiber via an opening, the optical fiber extending through the opening.

In another exemplary aspect of the present disclosure, the OCT probe may include a cannula having a lumen. The cannula may also include a cannula axis. The OCT probe may also include a selectively displaceable light-carrying optical fiber disposed within the lumen of the cannula and having a distal end. The optical fiber may be adapted to emit light from the distal end. A flexor may include a first segment and a second segment extending through the lumen and may have an opening formed therein through which the optical fiber extends. A driver may be configured to axially displace at least one of the first segment and the second segment to cause said one of the first segment and the second segment to elastically bow and laterally displace the optical fiber.

In an aspect, the flexor may include a tubular portion. The second segment may extend through the tubular portion. In an aspect, the tubular portion of the first segment may be fixed in place relative to the cannula. In an aspect, the driver may be adapted to axially displace the first segment to cause the optical fiber to become laterally displaced.

In an aspect, this disclosure is directed to a method of scanning with an OCT probe. The method may include emitting a light at patient tissue from an optical fiber in a lumen of a cannula of the OCT probe. The method may also include laterally displacing the optical fiber within the lumen of the cannula in response to axial displacement of a portion of the flexor coupled to the optical fiber.

In an aspect, the optical fiber extends through an opening in the flexor. In an aspect, the flexor may include a first segment, a second segment, and a tubular portion. The first segment may extend through the tubular portion.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

For the purposes of promoting an understanding of the principles of the present disclosure, reference will now be made to the exemplary embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

The present disclosure relates generally to OCT probes, OCT systems, and methods that scan tissue to obtain an OCT image. The probe includes a cannula configured to invasively penetrate patient tissue, such as the globe of an eye. The cannula houses a lens and an optical fiber. The optical fiber directs light through the lens and captures reflected light that passes back through the lens. To obtain a scan of an area or a line of tissue, rather than merely a point, at least a portion of the fiber moves back and forth within the cannula relative to the lens, and the light emerging from the lens is deviated angularly. Because the cannula that penetrates the patient tissue is desirably small in cross-section, moving the fiber within the cannula poses challenges.

Exemplary aspects described herein utilize a technique of laterally moving at least the end of the fiber within the cannula using a flexor. The flexor extends from a location along a distal portion of the fiber to a proximal location that may be disposed outside the cannula, such as in a probe housing. The fiber may then be laterally displaced by pulling or pushing the flexor that acts on a side of the fiber to laterally displace the fiber. The flexor elastically bows or flexes to impart a force in a lateral direction that displaces the fiber.

Figure 1:
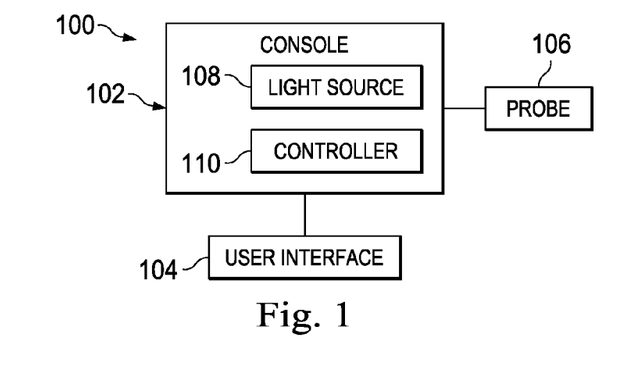
FIG. 1 is a block diagram of an exemplary OCT imaging system.

FIG. 1 shows an exemplary example of an OCT imaging system 100. The system 100 includes a console 102, a user interface 104, and an OCT probe 106. The console 102 includes an OCT engine including, among other elements, a light source 108 and a controller 110. The light source 108 is configured to provide near-infrared (NIR) light reflected and captured from the target biological tissue through the OCT probe 106. In other implementations, radiation having other frequencies may be used. Any defined bandwidth of light frequencies may be used with OCT. For many ophthalmic applications, near-infrared may be used. For example, radiation bandwidth frequencies of 700 to 900 nm with a center wavelength of 800 nm may be used in some ophthalmic applications. In other instances, a radiation wavelength band of 1250-1450 with a center wavelength of 1350 nm may be used. Still further, a radiation wavelength band of 1400-1600 with a center wavelength of 1500 nm may be used. Further, while examples provided herein may be described in the context of ophthalmic procedures, the scope of the application is not so limited. Rather, the concepts presented herein may also be used in other applications. For example, the concepts may be used in other medical procedures. Still further, the concepts described herein may be used in any other suitable area. Particularly, the concepts described may be used in areas outside of the medical arts.

In some embodiments, the light source 108 may include super-luminescent diodes, ultra-short pulsed lasers, or super-continuum lasers that provide relative long wavelength light. The controller 110 may include a processor and memory that may include an executable program for operating the light source 108, the user interface 104, and the OCT probe 106, and for executing and performing functions and processes to carry out an OCT imaging procedure. In some implementations, the light source 108 may produce (NIR) light may be in the range of 700 to 900 nm, 1250 to 1450 nm, and 1400 to 1600 nm. Particularly, in some implementations, the light source 108 may produce NIR light having wavelength bands having center frequencies of 850 nm, 1060 nm, or 1350 nm. These frequency ranges are provided merely as examples, and the disclosure is not intended to be limited thereto. Rather, the concepts used herein may include radiation wavelengths of any desired frequency or range of frequencies.

In some embodiments, the user interface 104 is carried on or forms a part of the console 102. The user interface 104 may be a display configured to present images to a user or a patient, and display tissue scanned by the probe 106 during an OCT imaging procedure. The user interface 104 also may include input devices or systems including, by way of non-limiting example, a keyboard, a mouse, a joystick, dials, and/or buttons, among other input devices.

The OCT probe 106 is sized and shaped to be handled by a user, such as a surgeon or other medical professional, and to protrude into a body of the patient. In the embodiment shown, the OCT probe 106 is in electrical and optical communication with the console 102 and configured to present light from the light source 108 onto patient tissue for the purpose of imaging the tissue.

Figure 2:
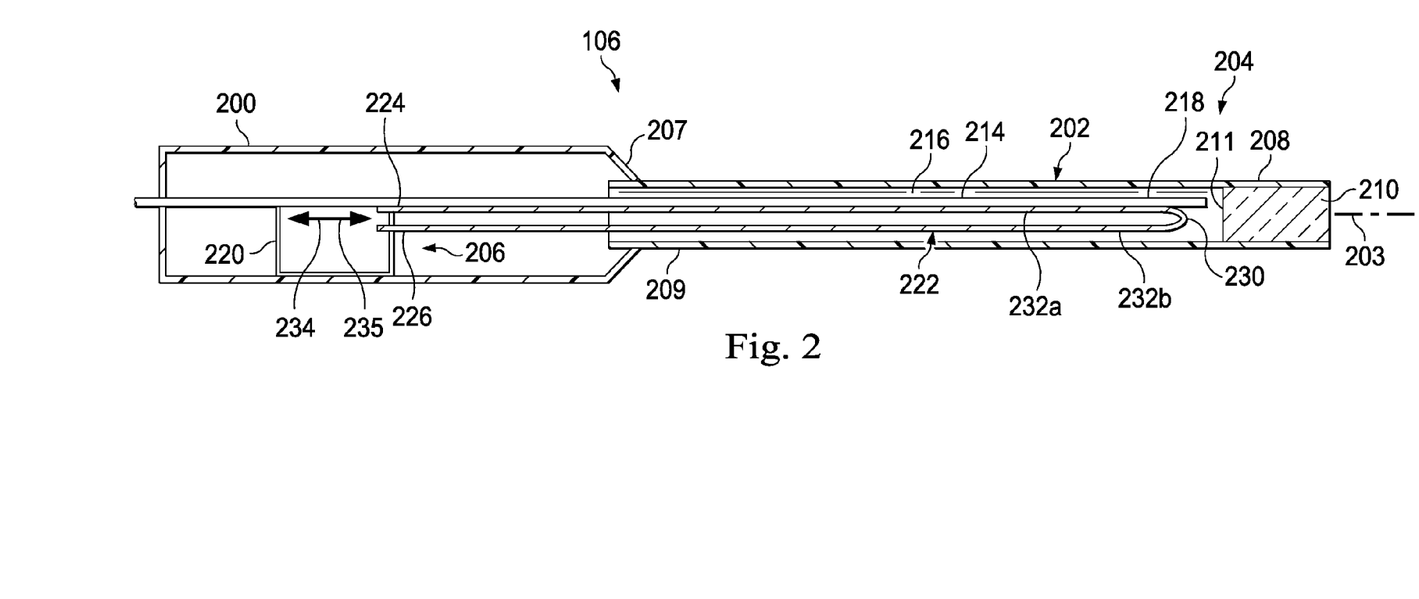
FIG. 2 is a cross-sectional view of an example OCT probe.

FIG. 2 shows an example OCT probe 106. As will be described in greater detail below, the OCT probe 106 includes a mechanism for displacement of an optical fiber carrying light from the light source 108 in a manner that moves the fiber relative to a lens. Light from the optical fiber deflects through the lens, causing the light beam to deflect angularly. An angular scan is produced by moving the position of the fiber laterally with respect to a lens, such as lens 210 described below.

Still referring to FIG. 2, the OCT probe 106 includes a probe housing 200, a cannula 202, a lighting system 204, and an actuation system 206. The probe housing 200 is configured to be grasped and manipulated by a user, such as during an OCT procedure. A portion of the housing 200 may form a handle or grip and may house components of the OCT probe 106. The probe housing 200 includes a distal end 207 from which the cannula 202 projects. The cannula 202 includes a central axis 203 and is configured and arranged to penetrate patient tissue in order to obtain an OCT image.

The cannula 202 includes a distal end 208 and a proximal end 209. The proximal end 209 of the cannula 202 is disposed within and supported by the probe housing 200. In some embodiments, a lumen 216 of the cannula 202 receives a portion of the actuation system 206 and the lighting system 204 in the manner described below. In some instances, the cannula 202 may be sized to penetrate and be used within an eye and may be used to scan tissue of a patient. For example, in some instances, the cannula 202 may be utilized to scan eye tissue of a patient, such as retina tissue.

The lighting system 204 includes lens 210 and an optical fiber 214. The lighting system 204 receives and transmits light from the light source 108. In some implementations, the lens 210 may be a gradient index (GRIN) lens having flat surfaces through which light from the optical fiber 214 may pass. In some implementations, the gradient index may be spherical, axial, or radial. Thus, in other instances, the lens 210 may be a spherical lens. In still other instances, a lens having other shapes may be used.

The optical fiber 214 is configured to transmit light from the light source 108 to the lens 210, and ultimately to the tissue under observation. In some implementations, the optical fiber 214 may be is a single fiber. In other instances, the optical fiber 214 may be a bundle of optical fibers. In some instances, the optical fiber 214 may be a continuous optical fiber extending from the light source 108 to distal end 218 of the optical fiber 214. In other instances, the optical fiber 214 may be formed from two or more optical fibers extending from the light source 108. Further, in still other implementations, the optical fiber 214 may receive light from the light source 108 from an optical fiber extending from the console 102 to the OTC probe 106.

In some instances, a proximal end (not shown) of the optical fiber 214 may be disposed adjacent the light source 108 (FIG. 1), while a distal end 218 may be disposed adjacent the lens 210 in a manner directing light through the lens 210. As shown in FIG. 2, the optical fiber 214 is not directly connected to the lens 210, and the lens 210 is fixed in place relative to the cannula 202. Accordingly, the optical fiber 214 may move relative to the cannula 202 and the lens 210. The distal end 218 of the optical fiber 214 may be positioned a pre-determined distance from a face 211 of the lens 210 to achieve, for example, a desired optical focal length through the lens 210.

The actuation system 206 may include a driver 220 and a displacement member, shown as a flexor 222. The actuation system 206 is operable to laterally move the optical fiber 214 relative to the cannula 202 in order to provide either one or two dimensional directional scanning to create 2D or 3D images with the OCT imaging system 100. The actuator system 206 is operable to displace the flexor 222 in the direction of arrows 234 and/or 235. The flexor 222, in turn, is operable to displace at least a portion of the optical fiber 214 laterally relative to the cannula 202 and the lens 210.

Moreover, the flexor 222 is operable to displace the optical fiber 214 in a way so as to minimize any change in distance between the distal end 218 of the optical fiber 214 and a proximal end 211 of lens 210. In some implementations, this minimal change in distance between the distal end 218 of the optical fiber 214 and the proximal end 211 of the lens 210 is due to the small angular articulation of the optical fiber 214 relative to the lens 210.

The driver 220 may be a microelectrical mechanical systems (MEMS) micromoter, a linear motor, a piezoelectric motor, an electromagnetic motor, a pneumatic piston, diaphragms, electrical solenoid, or other element or mechanism. For example the driver 220 may be any device or mechanism operable to displace the flexor 222 in the directions of arrows 234, 235. The driver 220 is configured to impart a force on the flexor 222 to physically displace the flexor 222 along the axial direction of the fiber, as indicated by the arrows 234, 235 associated with the flexor 222 in FIG. 2. In some embodiments, the driver 220 is electrically powered and is electrically connected to the console 102 by a power cable (not shown) extending from the OCT probe 106. In other embodiments, the driver 220 is disposed in the probe housing 200 and is configured to be self-contained. Accordingly, in some implementations, the driver 220 may include a power source that provides power to the driver 220 to physically displace the flexor 222 to move the optical fiber 214 within the cannula 202. In some implementations, the power source may be disposed in or on the housing 200. In some implementations, the power source may be or include a battery. In some implementations, the driver 220 may be configured to displace the flexor 222 in a back and forth motion by applying force or loading on flexor 222 in order to create a deflecting force on the optical fiber 214. For example, the driver 220 may be arranged to reciprocatingly drive the flexor 222 in the directions of arrows 234, 235, as explained below.

The flexor 222 may be formed of an elastically deflectable material. For example, in some implementations, the flexor 222 may be formed of a metal or alloy, such as stainless steel. Some alloy implementations include shape-memory alloys, such as nitinol. Other materials are also contemplated. In the embodiment shown in FIG. 2, the flexor 222 is folded and includes a crease or bend 230 forming a distal-most portion of the flexor 222. Being folded, the flexor 222 includes two segments 232a, 232b extending from the bend 230 in the proximal direction within the cannula 202. Ends 224, 226 of the flexor 222 are disposed adjacent the driver 220 and are adapted to be actuated by the driver 220 in a direction substantially parallel to the direction of the optical fiber 214 and the cannula axis 203, as indicated by the arrows 234, 235. In the example shown, the flexor 222 is sufficiently rigid to support the optical fiber 214 within the cannula 202 without additional anchors or supports. Accordingly, the flexor 222 is adapted to support the fiber 214 in the cannula 202.

As shown in FIG. 2, the segment 232a is disposed adjacent the optical fiber 214 and is coupled thereto. The segment 232a may be coupled to the optical fiber 214 at one or more locations proximate the bend 230. In some implementations, the segment 232a may be coupled to the fiber 214 along substantially an entire length of the segment 232a. In other implementations, only a distal portion of the segment 232a may be coupled to the optical fiber 214. The segment 232b projects at an oblique angle away from the optical fiber 214 at the bend 230 and then curves in the proximal direction toward the driver 220.

Figure 3:
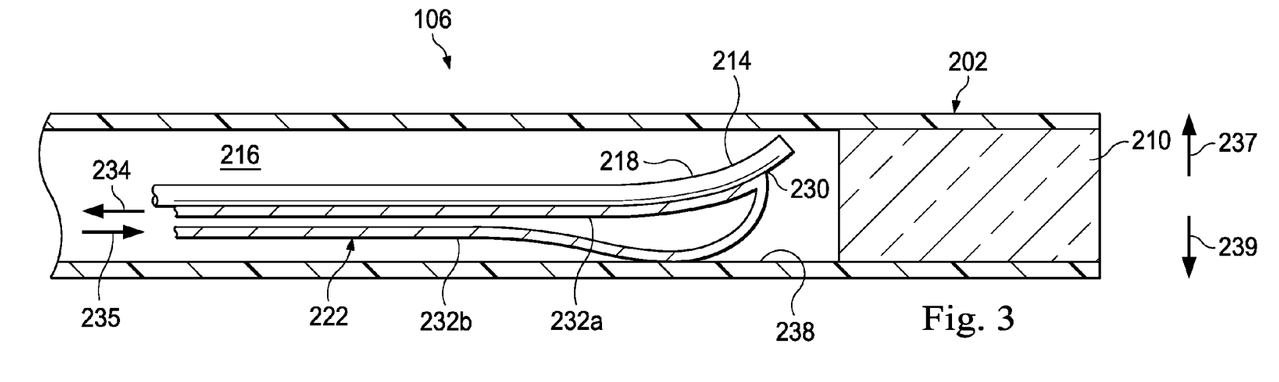
FIG. 3 is a cross-sectional detail view of the example OCT probe shown in FIG. 2.
Figure 4:
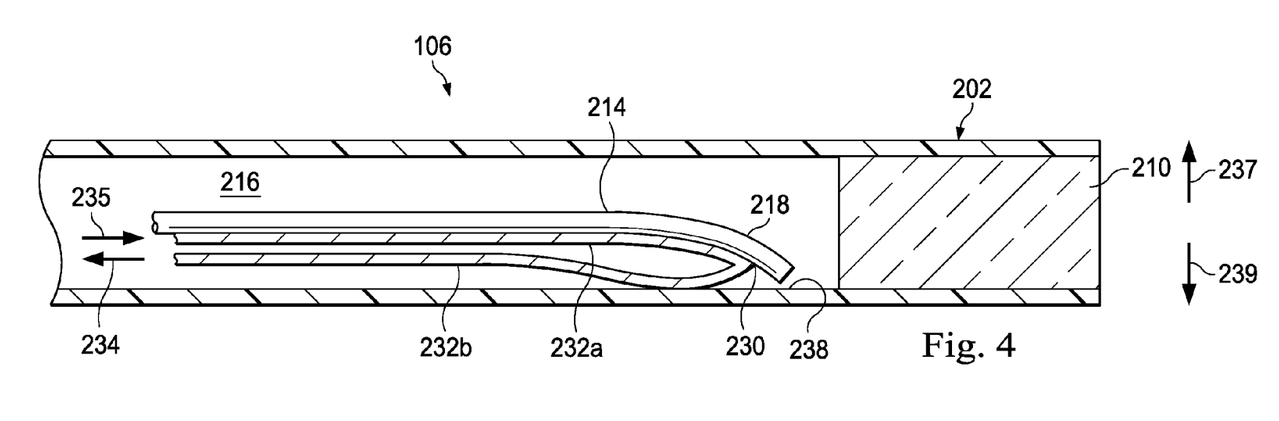
FIG. 4 is a cross-sectional detail view of the example OCT probe shown in FIG. 2.

FIGS. 3 and 4 illustrate movement imparted to the optical fiber 214 by movement of the segments 232a, 232b of the flexor 222 in the indicated directions of arrows 234, 235. Movement of the optical fiber 214 as shown in FIGS. 3 and 4 represent scanning motion that may be utilized in an OCT scanning operation. Bowing of the flexor 222 causes a corresponding bowing or bending of the optical fiber 214. As a result of the bending of the optical fiber 214, the distal end 218 of the optical fiber 214 extending beyond the location of the optical fiber 214 in contact with the flexor 222 is displaced. Thus, the distal end of the optical fiber 214, may be displaced in lateral directions indicated by arrows 237, 239 within the cannula 222 to perform a scan cycle. In some implementations, a distal portion of the optical fiber 214, may be displaced within the cannula 222 in the directions indicated by arrows 237, 239 to perform a scan cycle. Referring first to FIG. 3, the driver 220 pushes the segment 232b in the direction of arrow 235 and pulls the segment 232a in the direction of arrow 234). This causes the segment 232b to elastically bow outwardly and, in the exemplary example shown, engage against the inner cannula wall 238. In some embodiments, the inner cannula wall 238 may act as a stable support or brace against which the segment 232b engages. Further pushing causes the bowing segment 232b to displace the distal end of the optical fiber 214 in the direction of arrow 237 and in the manner shown in FIG. 3. Accordingly, the bowing or flexing of the flexor 222 creates the lateral movement that displaces the optical fiber 214. In other implementations, however, the flexor 222 may be operable to laterally displace the optical fiber 214 without the flexor 222 contacting the inner cannula wall 238.

FIG. 4 shows the same portion of the OCT probe 106 with the optical fiber 214 displaced in the opposite direction from that shown in FIG. 3. Here, the driver 220 pulls the segment 232b in the direction of arrow 234 and pushes the segment 232a in the direction of arrow 235 to pull, rather than push the distal end 218 of the optical fiber 214. This moves the optical fiber 214 laterally in the direction of arrow 239 across the lumen 216 of the cannula 202 to provide an OCT scan. As can be seen, the optical fiber 214 is driven in the direction of arrow 239, opposite the direction of arrow 237 shown in FIG. 3. The lateral scan distance, i.e., the amount of lateral displacement experienced by a portion of the optical fiber 214 (e.g., the distal end 218), is related to the location of the bend 230 relative to the distal end 218 of the optical fiber 214 and the angular bowing of the flexor 222. Movement of the flexor 222 causes bending or bowing of the optical fiber 214 along a length of the optical fiber 214 proximate the location of the bend 230. This bowing of the optical fiber 214 displaces the distal end 218 in the directions of arrows 237 and 239.

In some implementations, the controller 110 is configured to control the driver 220 to actuate the optical fiber 214 by axially pulling or pushing on the segments 232a, 232b. In some implementations, the driver 220 may operate within a frequency range of about 1 to 30 Hz, although other frequency ranges, both larger and smaller, are contemplated.

Figure 5:
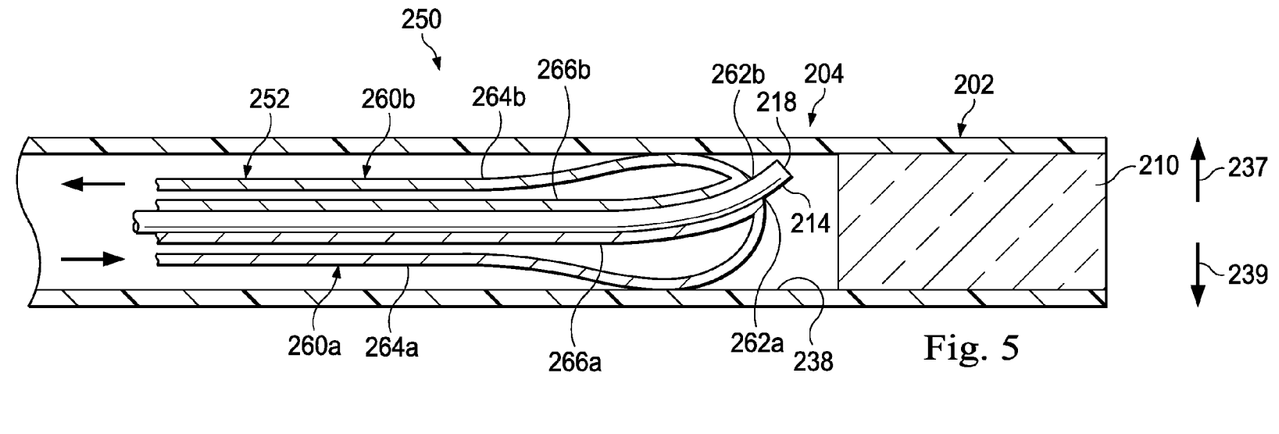
FIG. 5 is a cross-sectional detail view of another example exemplary OCT probe.

FIG. 5 shows a distal end region of another example OCT probe 250 having an actuation system 252. Similar to the OCT probe 106, the OCT probe 250 includes a cannula 202 and a lighting system 204. The lighting system 204 includes a lens 210 and an optical fiber 214. The OCT probe 250 also includes an arrangement of flexors 260a, 260b disposed on opposing sides of the optical fiber 214. In some implementations, the flexors 260a, 260b may be similar to the flexor 222 described above. In the illustrated example, each flexor 260a, 260b includes a bend and two extending segments that meet at the bend. Particularly, flexor 260a includes a bend 262a and segments 264a, 266a, and flexor 260b includes a bend 262b and segments 264b, 266b. In some implementations, the bend 262 may be in the form of a bend or crease. However, unions of other configurations are within the scope of the disclosure. The segments 266a, 266b are disposed against the optical fiber 214, and segments 264a, 264b are disposed between the segments 266a, 266b and the cannula inner wall 238. In some implementations, with two flexors 260a, 260b acting on opposite sides of the optical fiber 214, a driver, which may be similar to driver 220, acts to push or pull the segments 264a, 264b, and the elastic flexing of the segments 266a, 266b creates the lateral force to displace the fiber 214 in the directions of arrows 237, 239. Similar to the examples described above, this lateral movement of the optical fiber 214 is utilized to perform a tissue scan. That is in some implementations, the driver 220 does not act directly on segments 266a, 266b. As such, segments 266a and 266b may have lengths sufficient to couple to the optical fiber 214. In some implementations, the segments 266a, 266b coupled to the optical fiber 214 may have a length shorter than the length of segments 264a, 264b. The segments 264a, 264b may extend only far enough to secure the flexors 260a, 260b to the optical fiber 214. As such, in some instances, the segments 266a, 266b do not couple to a driver. Further, in some instances, the segments 266a, 266b may not extend into a housing of the OCT probe 250, such as a housing similar to housing 200. In other implementations, one or more drivers, which may be similar to driver 220 described above, may be operable to act on both the segments 266a, 266b as well as 264a, 264b. In such implementations, operation of the one or more drivers is coordinated so as to laterally displace a portion of the optical fiber 214, such as, in some instances, the distal tip 218 of the optical fiber 214.

Figure 6:
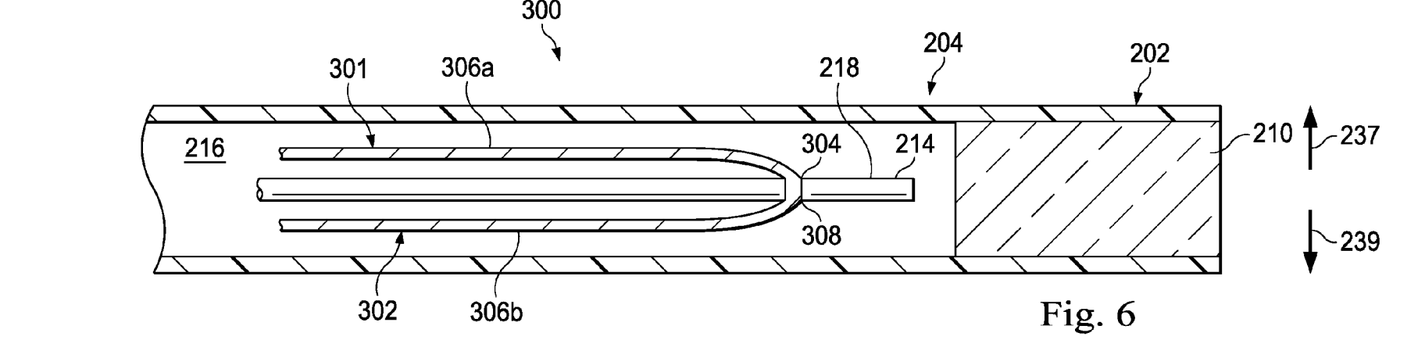
FIG. 6 is a cross-sectional detail view of another example OCT probe.
Figure 7:
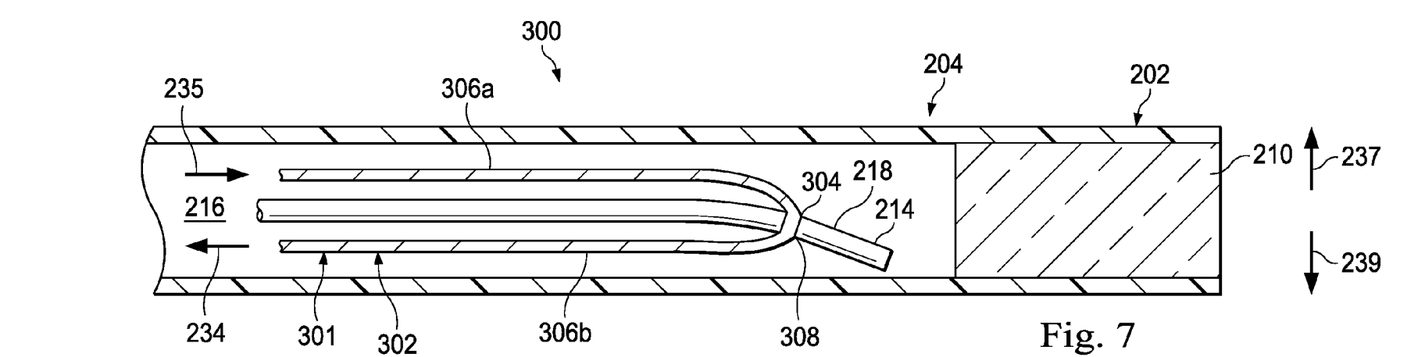
FIG. 7 is a cross-sectional detail view of another example OCT probe.

FIGS. 6 and 7 show a distal end region of another example OCT probe 300. The OCT probe 300 may be similar to one or more of the OCT probes described herein and includes an actuation system 301, a cannula 202, and a lighting system 204. Also similar to the OCT probes described above, the lighting system 204 of the OCT probe 300 may include a lens 210 and an optical fiber 214. The actuation system 301 includes a flexor 302 having segments 306a and 306b disposed on opposing sides of the optical fiber 214. Lateral movement in the directions of arrows 237, 239 of a distal portion of the optical fiber 214 (e.g., the distal end 218 of the optical fiber 214) is effectuated by actuating the segments 306a and 306b in opposing directions. For example, to laterally displace the optical fiber 214 in the direction of 239, the segment 306b is displaced in the direction of arrow 234, and the segment 306a is displaced in the direction of 235. To displace the optical fiber 214 in the direction of arrow 237, the segments 306a, 306b are displaced in the opposite directions. In some implementations, the flexor 302 may be similar to the flexor 222. For example, flexor 302 may have mechanical characteristics and/or be formed from materials similar to the flexors 222. Also, similar to the flexor 222, the flexor 302 includes a bend 304 that divides the flexor 302 into the two segments 306a, 306b. In this example, though, the fiber 214 extends through an opening 308 formed in the flexor at the bend 302. Consequently, the segments 306a and 306b are disposed on opposite sides of the fiber 214. In some implementations, the two segments 306a, 306b may be separate members that are bonded together at the bend 304. In still other implementations, the flexor 302 may be a unitary component.

FIG. 6 shows the optical fiber 214 in a neutral condition, while FIG. 7 shows the optical fiber 214 in a deflected or displaced condition. Also similar to the OCT probes described above, the OCT probe 300 includes a driver. The driver may be similar to the driver 220 described above. As explained previously, the driver is operable to displace the segment 306a in the direction of arrow 235 and the segment 306b in the direction of arrow 234 causing the optical fiber 214 to deflect in the direction of arrow 239, as shown in FIG. 7. When the driver actuates to displace the segment 306a in the direction of arrow 234 and the segment 306b in the direction of arrow 235, the optical fiber 214 is deflected in the opposite direction, i.e., in the direction of arrow 237. Thus, the segments 306a, 306b elastically bow or flex to create the lateral movement that displaces the fiber 214 within the lumen 216 of the cannula 202 to enable scanning even in the small confines of the cannula 202.

Figure 8:
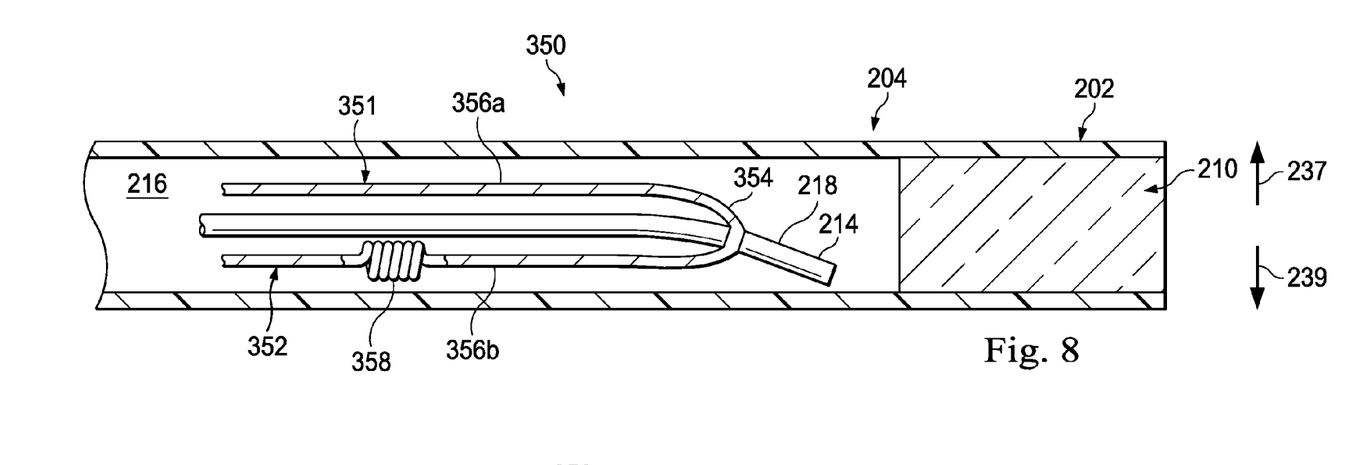
FIGS. 8 and 9 are cross-sectional detail views of another example OCT probe.
Figure 9:
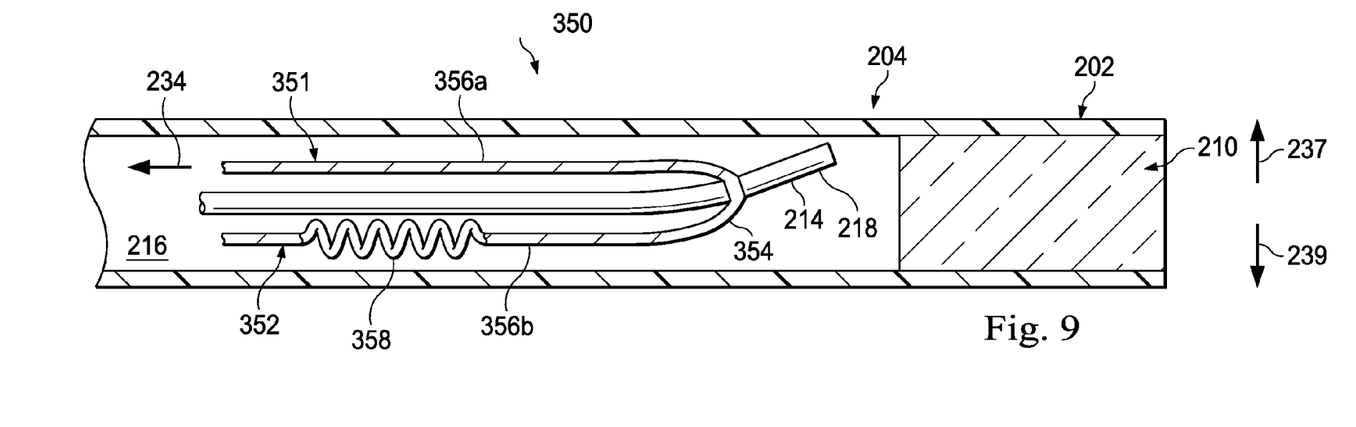

FIGS. 8 and 9 show a distal end region of another example OCT probe 350. The OCT probe 350 may be similar to one or more of the OCT probes described herein and includes an actuation system 351, a cannula 202, and a lighting system 204. The lighting system 204 may include a lens 210 and an optical fiber 214. The actuation system 351 includes a flexor 352 disposed on opposing sides of the fiber 214. The OCT probe 350 may also include a driver to drive the flexor 352. The driver may be similar to one or more of the drivers discussed above.

The flexor 352 may be similar to the flexor 302 described above. As such, the flexor 352 is operable to elastically bow or flex and support the optical fiber 214 within the cannula 202. In addition, the flexor 352 includes a bend 354 dividing the flexor 352 into two segments 356a, 356b. In this example, the segment 356b includes a biasing element 358. In some implementations, the biasing element 358 may be in the form of a coil spring. The biasing element 358 provides a biasing force on the flexor 352, flexing the optical fiber 214 off-center toward a deflected position. For example, as shown in FIG. 8, the biasing element 358 deflects the optical fiber 214 in the direction of arrow 239.

FIG. 8 shows the OCT probe with the biasing element 358 in a substantially neutral condition in which a portion of the optical fiber 214 is displaced in the direction of arrow 239. In some instances, the distal end 218 of the optical fiber 214 is displaced laterally. In other instances, a different portion of the optical fiber 214 is laterally displaced.

In some instances, the segment 356a may be initially in tension when the actuation system 351 is in an unactuated condition. Thus, in such instances, at rest, the distal end 218 of the optical fiber 214 may be deflected in the direction of arrow 239. Referring to FIG. 9, as force in the direction of 234 is applied to segment 356b, the biasing element 358 is expanded, pivoting the distal end 218 of the optical fiber 214 in the direction of arrow 237. FIG. 9 shows the OCT probe with axial loading on the segment 356a, elastically deflecting the optical fiber 214 in the direction of arrow 237. Thus, to move the optical fiber 214 in the direction of arrow 237, the segment 356a is displaced in the direction of arrow 234. As the segment 356a is displaced in the direction of arrow 234, at least a portion of the optical fiber 214 is caused to sweep in the direction of arrow 237. As a result of this displacement of the optical fiber 214, the biasing element 358 is loaded so as to resist movement of the optical fiber 214. Release of the segment 356a causes the biasing element 358 to return the optical fiber 214 to the position shown in FIG. 8.

In operation, such as during a scanning procedure, the driver axially loads the segment 356a in the direction of arrow 234. As a result, the biasing element 358 is elastically stretched from the condition in FIG. 8 to the condition in FIG. 9. When the optical fiber 214 is laterally displaced as a part of the scan, the driver may decrease the loading on the segment 356a. The biasing element 358 then retracts toward its neutral condition, and pulls the optical fiber 214 from one side of the cannula 202 toward the position shown in FIG. 8. Thus, the driver may actuate on only a single segment of the flexor 352. In addition, the driver 220 may be a single-acting actuator, meaning the driver 220 actuates in only a single direction.

In some implementations, such as the example shown in FIG. 8, when in the neutral condition, the biasing element 358 does not apply a biasing force. In other implementations, the biasing element may provide a biasing force even when the optical fiber is in the lateral position shown in FIG. 8. It should also be recognized that, although the biasing element 358 is shown within the lumen 216 in FIGS. 8 and 9, in other implementations, the biasing element 358 may be disposed outside of the cannula 202. For example, in some implementations, the biasing element 358 may be disposed outside of the lumen 216 and in the probe housing.

Figure 10:
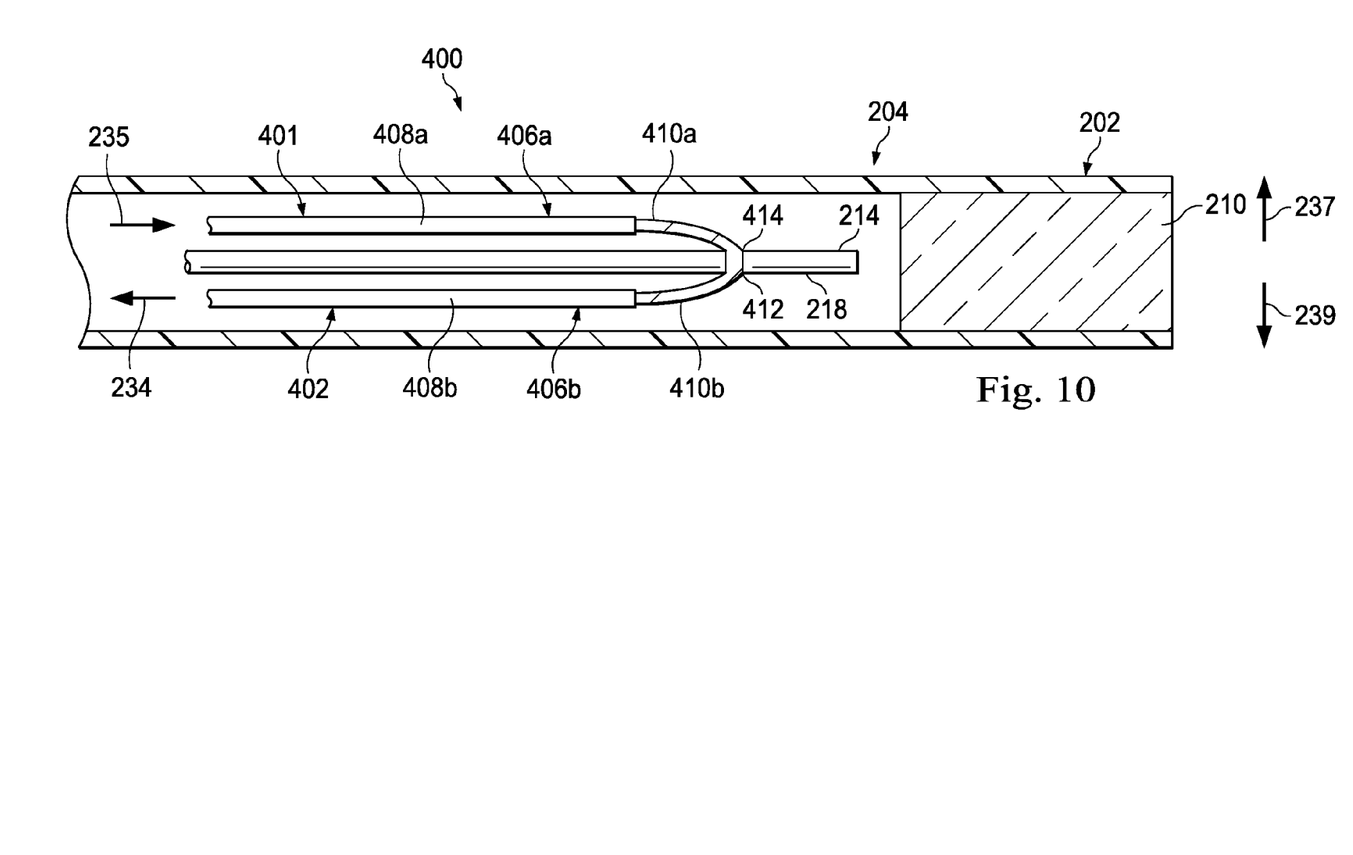
FIG. 10 is a cross-sectional detail view of another example OCT probe.

FIG. 10 shows a distal end region of another example OCT probe 400. The example OCT probe 400 may be similar to one or more of the OCT probes described herein and includes an actuation system 401, a cannula 202, and a lighting system 204. The lighting system 204 includes a lens 210 and optical fiber 214. The actuation system 401 includes a flexor 402 having segments 406a, 406b that extend along opposing sides of the optical fiber 214. The flexor 402 may be similar to the flexor 352. Each segment 406a and 406b respectively includes a rigid portion 408a, 408b and a flexible portion 410a, 410b. The flexible portions 410a, 410b intersect at a crease or bend 412 that includes an opening 414 through which the optical fiber 214 extends. The rigid portions 408a, 408b extend between the flexible portions 410a, 410b and the driver, which may be of a type similar to driver 220 described above. The rigid portions 408a, 408b provide stability to the flexor 352 to ensure a high level of control and repeatability. The flexible portions 410a, 410b elastically bow or flex to create the lateral movement that displaces the at least a portion of the optical fiber 214. In some instances, the distal end 218 may be laterally displaced. In addition, the flexor 402 may provide support to the optical fiber 214 in the cannula 202. Accordingly, the driver 220 may push and pull the rigid portions 408a, 408b in the directions of arrows 234 and 235 in a manner similar to that described above, for example, in the context of the OCT probe 300 shown in FIGS. 6 and 7, to move the distal end portion 118 of the fiber 214 in a lateral directions 237, 239 to perform an OCT scan procedure.

In some implementations, the optical fiber 214 may extend in the distal direction between about 3 and 20 mm beyond the flexor. In some implementations, the flexor is arranged to laterally displace or pivot at least a portion of the optical fiber 214 within the cannula 202 within a range of about 0.5 to 5 degrees. In some implementations, the flexor is operable to pivot at least a portion of the optical fiber 214 within a range of about 0.5 to 3 degrees. In some implementations, such a pivoting capability provides about a 3 to 4 mm scan of a location on which the OCT probe 400 is focused. However other pivot ranges and other scan ranges are contemplated.

While the various examples illustrated and discussed herein show the distal end 218 of the optical fiber 214 laterally displaced in order to perform an OCT scan, the scope of the disclosure is not so limited. That is, in some implementations, a portion of optical fiber 214 greater than the distal end 218 may be laterally displaced according to the principles disclosed herein. Thus, even though one or more of the examples may describe or show lateral movement of the distal end 218 of the optical fiber 214, these are provided merely as examples, and the scope of the disclosure is not so limited.

In some implementations, the optical fiber 214 is sized to extend distally far beyond the flexor. This may limit the rotation of the optical fiber 214 in the cannula 202. Particularly, the longer the distance the optical fiber 214 extends beyond the flexor, the smaller the angle that the optical fiber 214 travels to achieve the same lateral displacement. That is, a smaller angle corresponds to a smaller displacement of the flexor (e.g., a segment of the flexor) in the direction along the central axis 203 of the cannula 202. In some aspects, a small displacement may be desirable, as a large displacement may change the focal point of the OCT system 100 and affect the quality of the OCT performance. In addition, the amount by which the optical fiber 214 extends beyond the flexor may limit changes in the size of a gap between the distal end 218 of the optical fiber 214 and the lens 210 as the optical fiber 214 is displaced. Here, the gap distance between the distal tip 218 of the optical fiber 214 and the lens 210 may be within a range of up to and greater than about 500 microns. In other instances, the range may be within about 150 to 500 microns. In yet other instances, the range is about 150 to 200 microns. Other ranges are contemplated.

Figure 11:
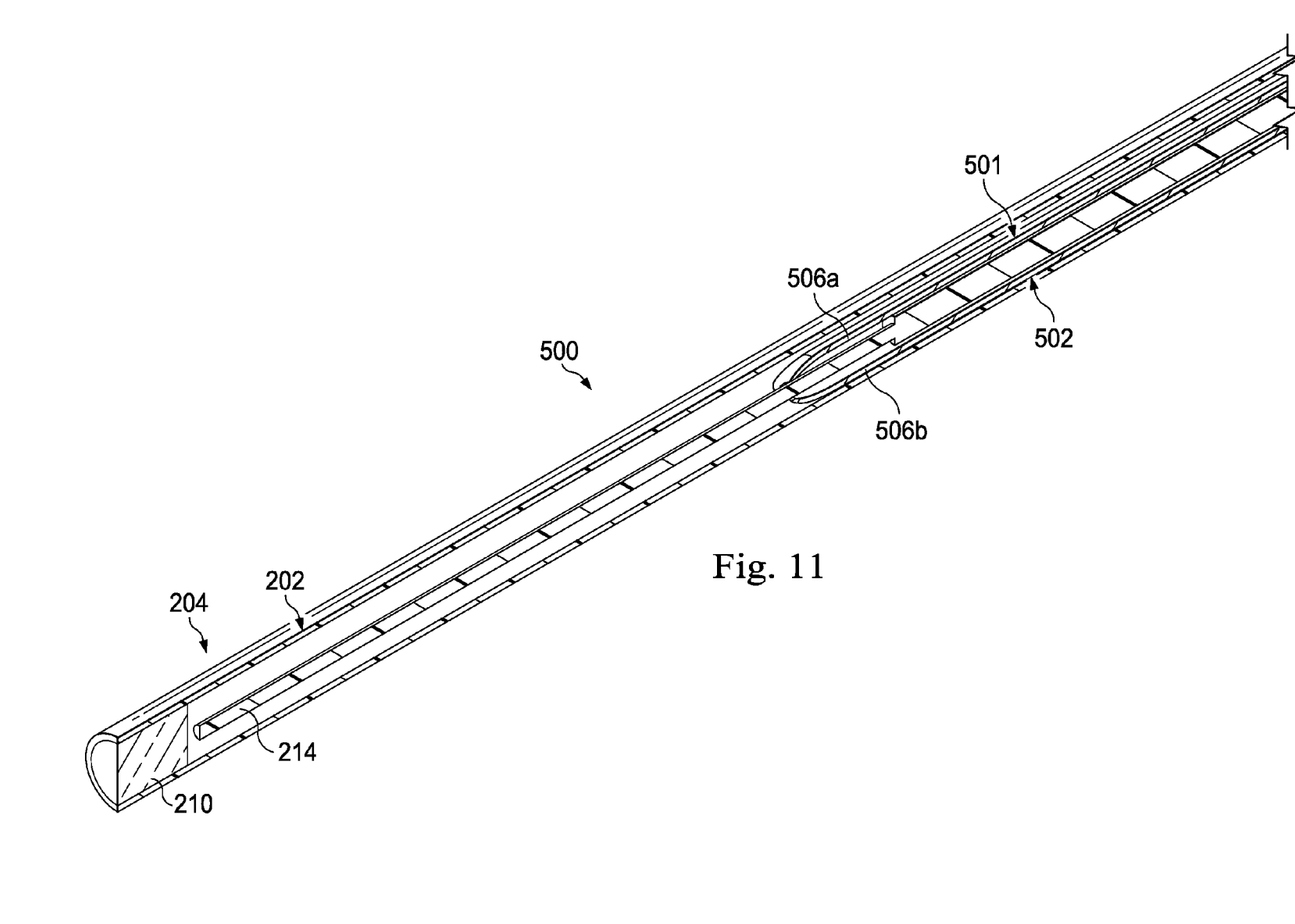
FIG. 11 is a perspective, cross-sectional view of another example OCT probe.
Figure 12:
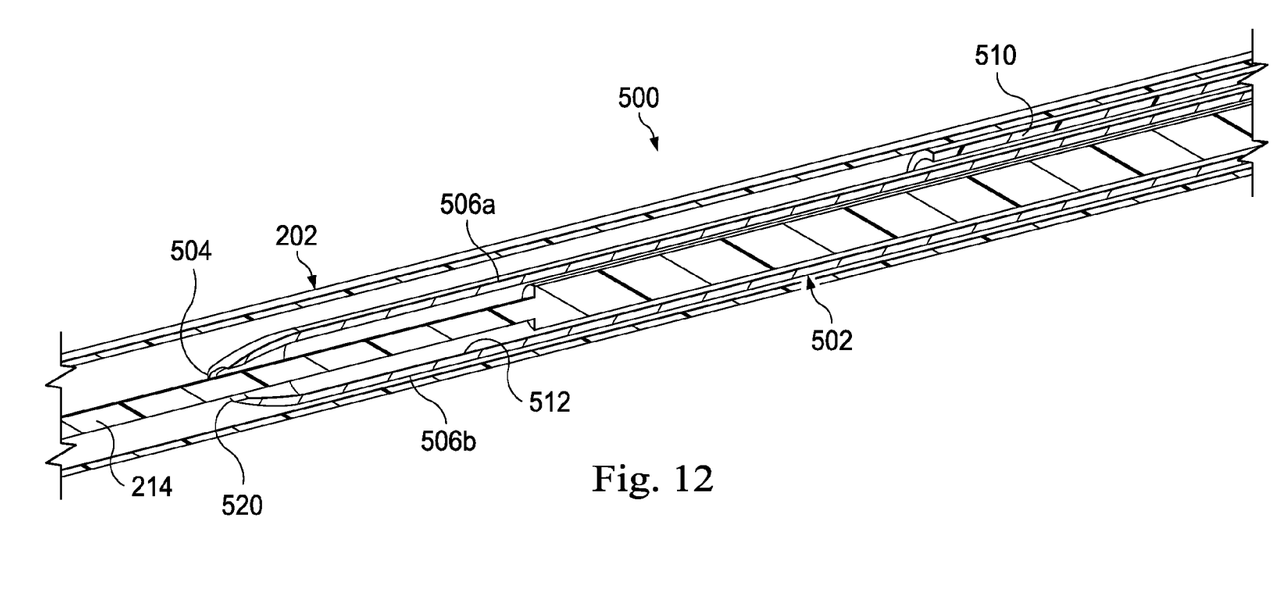
FIG. 12 is a detail view of a portion of the example OCT probe of FIG. 11.
Figures 13, 14:
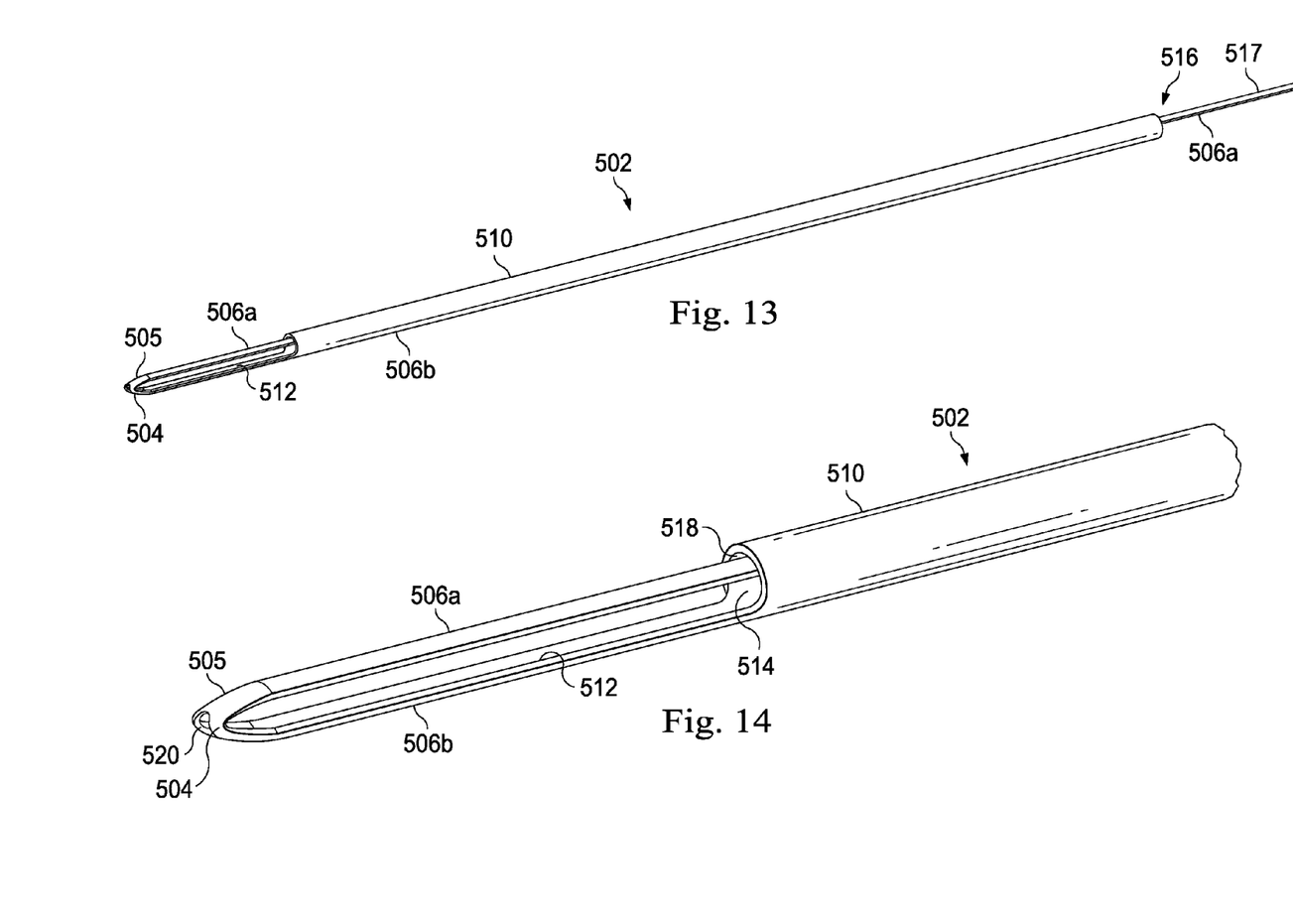
FIG. 13 is a perspective view of an example flexor.
FIG. 14 is a detail view of the example flexor of FIG. 13.

FIGS. 11-14 show portions of another example OCT probe 500. The OCT probe 500 may be similar to one or more of the OCT probes described herein and includes an actuation system 501, a cannula 202, and a lighting system 204. The lighting system 204 includes a lens 210 and an optical fiber 214. The OCT probe 500 also includes a flexor 502 that includes a tubular portion 510 and a strip flexor portion 512 extending from the tubular portion 510. The strip flexor portion 512 includes segments 506a, 506b disposed on opposing sides of the optical fiber 214. FIG. 11 shows the distal end of the probe 500 with the cannula 202. FIG. 12 shows the flexor 502 in the cannula 202 in greater detail. FIG. 13 shows the flexor 502 independent of other components of the probe 500, and FIG. 14 shows the distal end of the flexor 502 independent of other components of the probe 500.

Referring to FIGS. 11-14, the flexor 502 includes a bend 504 that divides the strip flexor portion 512 into the two segments 506a, 506b. The tubular portion 510 includes an inner lumen 514 extending from a proximal end 516 thereof to a distal opening 518. The segment 506b extends distally from the tubular portion 510.

The segment 506a extends proximally from the segment 506b at the bend 504. The segment 506a extends through the distal opening 518, into the inner lumen 514, and out the proximal end 516 of the tubular portion 510. The segment 506a includes a proximal end 517 adapted to interface with a driver, which may be of a type similar to driver 220 described above. As can be seen in FIG. 14, an opening 520 is formed at the bend 504. The opening 520 permits passage of the optical fiber 214. The segments 506a, 506b are structurally configured to elastically bow or flex to create the lateral movement that displaces the optical fiber 214. In addition, the material characteristics of the flexor 502 support the optical fiber 214 in the cannula 202.

In some implementations, the flexor 502 is formed of a flat material that formed to create the segments 506a, 506b, the tubular portion 510, and the strip flexor portion 512. For example, in some instances, the flat material may be cut in the course of forming the flexor 502. Once cut, the opening 520 may be formed through the material (e.g., such as by a punching process), and sides may be rolled to create the tubular portion 510. The strip flexor portion 512 may include a bend or fold proximate the opening 520, and fed through the lumen 514 of the tubular portion 510. In some implementations, the flat material may be bent at the opening 520 to form the bend 504 prior to rolling the material to create the tubular portion 510. In such instances, the tubular portion 510 may be formed about the segment 506a so that the segment 506a protrudes from the proximal end 516 of the segment 506b.

In other implementations, the flexor 502 may be formed by laser cutting a round tube to form the strip flexor portion 512. The remaining portion of the round tube forms the tubular portion 510. The opening 520 may be formed strip flexor portion 512 by a punch or a laser cut, for example. The strip flexor portion 512 may be include a bend proximate the location of the opening 520, thereby dividing the strip flexor portion 512 into the segment 506a and the segment 506b. The segment 506a may be introduced into the lumen of the tubular portion 510.

While the illustrated example are shown as having the lens 210 fixed in place relative to the cannula 202, other implementations may have the lens 210 in a fixed spatial relationship with the distal end 218 of the optical fiber 214. Thus, in some instances, the optical fiber 214 and lens 210 may be bonded together. This optical arrangement may form the basis of an A-scan OCT in which the information is gathered at the single focal point. If the optical fiber 214 and lens 210 are then physically moved, a scan can be produced. Yet other implementations are contemplated.

In operation, a user controls the OCT probe at the console 102 and then orients the OCT probe at a location adjacent tissue to be evaluated. With the OCT probe at its desired location, the OCT probe is activated to begin a scanning procedure. To do this, the actuation system 206 operates to physically displace the optical fiber 214 relative to the lens 210 in a lateral back and forth motion. The flexor, such as a type of flexor described herein, structurally supports at least the distal portion the optical fiber 214 within the cannula 202. The flexor may support the distal portion of the optical fiber 214 without the use of pins or additional supporting structure. The driver 220 displaces at least a portion of the flexor by moving it in a direction substantially parallel to the axial direction of the optical fiber 214. Since the optical fiber 214 is coupled to the flexor, and due to the physical characteristics of the flexor itself, axial movement of the flexor creates an elastic bowing or flexing movement that moves the optical fiber 214 laterally back and forth within the cannula 202. This back and forth motion enables the optical fiber 214 to send and capture light over an area to create a scan. The controller 202 may then use the data to create a 3D image of the tissue being scanned.

In some implementations, including the example shown in FIGS. 11-14, one segment, a segment of a flexor, such as the tubular portion 510, may be fixed in place relative to the cannula 202. A driver, which may be of a type similar to driver 220 described above, may axially push and pull the segment 506a relative to the segment 506b to create a rocking effect at a distal end 505 of the flexor 502, thereby laterally moving the distal portion of the optical fiber 214 in the cannula 202 to create the scan.

Although the disclosure provides numerous examples, the scope of the present disclosure is not so limited. Rather, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An OCT probe for imaging patient tissue, comprising:
   a cannula comprising a lumen and having a cannula axis;
   a selectively displaceable light-carrying optical fiber disposed within the lumen and having a distal end, the optical fiber being adapted to emit light from the distal end;
   a flexor extending through the lumen and comprising a first segment and a second segment, the first segment coupled to the optical fiber; and
   a driver configured to linearly displace the second segment in a first axial direction that is parallel to the cannula axis such that the optical fiber is laterally displaced.

2. The OCT probe of claim 1, wherein the flexor comprises a bend, and wherein the second segment extends from the bend in an oblique direction.

3. The OCT probe of claim 2, wherein the second segment is configured to bow when the driver displaces the second segment in the first axial direction.

4. The OCT probe of claim 1, the flexor comprises a biasing element that cooperatively biases the fiber to a first position in the cannula.

5. The OCT probe of claim 1, comprising a second flexor extending through the lumen and comprising a third segment and a fourth segment, the third segment coupled to the optical fiber on a side of the optical fiber opposite the first segment.

6. The OCT probe of claim 5, wherein the driver is operatively coupled with the second segment and the fourth segment and configured to alternatingly displace one of the second segment or the fourth segment in the first axial direction and the other of the second segment or the fourth segment in a second axial direction opposite the first axial direction.

7. The OCT probe of claim 5, wherein the second flexor comprises a bend, and wherein the fourth segment extends from the bend in an oblique direction, and wherein the fourth segment is configured to bow when the fourth segment is displaced in one of the first axial direction or the second axial direction.

8. The OCT probe of claim 5, wherein the driver is configured to displace the second segment in the first axial direction while displacing the fourth segment in a second axial direction opposite the first axial direction to cause the optical fiber to be laterally displaced.

9. The OCT probe of claim 1, wherein the first segment is shorter than the second segment.

10. The OCT probe of claim 1, further comprising a lens disposed in the lumen of the cannula distal of the optical fiber and moveable with the fiber.

11. The OCT probe of claim 1, wherein the cannula is sized to penetrate an eye of a patient to scan a retina of the eye.

12. The OCT probe of claim 1, wherein the flexor comprises a tubular portion and the second segment extends through the tubular portion.

13. The OCT probe of claim 12, wherein the tubular portion is fixed in place relative to the cannula.

14. The OCT probe of claim 12, wherein the first segment is coupled to the optical fiber via an opening formed in the flexor, the optical fiber extending through the opening.

15. The OCT probe of claim 1, wherein the first segment extends along a portion of the optical fiber and is attached to the optical fiber along the portion of the optical fiber.

16. An OCT probe for imaging patient tissue, comprising:
    a cannula comprising a lumen and having a cannula axis;
    a selectively displaceable light-carrying optical fiber disposed within the lumen of the cannula and having a distal end, the optical fiber adapted to emit light from the distal end;
    a flexor comprising a first segment and a second segment extending through the lumen and having an opening formed therein through which the optical fiber extends; and
    a driver configured to linearly displace at least one of the first segment and the second segment in a first axial direction that is parallel to the cannula axis to cause said one of the first segment and the second segment to elastically bow and laterally displace the optical fiber.

17. The OCT probe of claim 16, wherein the flexor further comprises a tubular portion, and wherein the second segment extends through the tubular portion.

18. The OCT probe of claim 17, wherein the tubular portion of the first segment is fixed in place relative to the cannula.

19. The OCT probe of claim 18, wherein the driver is adapted to axially displace the first segment to cause the optical fiber to become laterally displaced.

20. A method of scanning with an OCT probe, comprising:
    emitting a light at patient tissue from an optical fiber in a lumen of a cannula of the OCT probe; and
    laterally displacing the optical fiber within the lumen of the cannula in response to a linear displacement of a portion of a flexor coupled to the optical fiber in an axial direction that is parallel to a longitudinal axis of the cannula, the flexor comprising a first segment and a second segment,
    wherein the first segment extends along a portion of the optical fiber and is attached to the optical fiber along the portion of the optical fiber.

* * * * *